(12) United States Patent
Stevens

(10) Patent No.: US 8,529,558 B2
(45) Date of Patent: Sep. 10, 2013

(54) HIGH-ORDER OPTICAL CORRECTION DURING CORNEAL LASER SURGERY

(75) Inventor: Julian D. Stevens, London (GB)

(73) Assignee: AMO Development LLC., Santa Ana, CA (US)

( * ) Notice: Subject to any disclaimer, the term of this patent is extended or adjusted under 35 U.S.C. 154(b) by 1175 days.

(21) Appl. No.: 12/428,293

(22) Filed: Apr. 22, 2009

(65) Prior Publication Data

US 2009/0292275 A1    Nov. 26, 2009

Related U.S. Application Data

(60) Provisional application No. 61/125,209, filed on Apr. 22, 2009.

(51) Int. Cl.
*A61B 17/22* (2006.01)

(52) U.S. Cl.
USPC ............................................... 606/5; 351/246

(58) Field of Classification Search
USPC .................. 606/4, 5; 351/211, 246
See application file for complete search history.

(56) References Cited

U.S. PATENT DOCUMENTS

| | | |
|---|---|---|
| 4,665,913 A | 5/1987 | L'Esperance, Jr. |
| 5,646,791 A | 7/1997 | Glockler |
| 5,683,379 A | 11/1997 | Hohla |
| 5,713,892 A | 2/1998 | Shimmick |
| 6,004,313 A | 12/1999 | Shimmick et al. |
| 6,095,651 A | 8/2000 | Williams et al. |
| 6,203,539 B1 | 3/2001 | Shimmick et al. |
| 6,271,915 B1 | 8/2001 | Frey et al. |
| 6,280,435 B1 | 8/2001 | Odrich et al. |
| 6,347,549 B1 | 2/2002 | Ryan et al. |
| 6,663,619 B2 | 12/2003 | Odrich et al. |
| 6,673,062 B2 | 1/2004 | Yee et al. |
| 7,130,835 B2 * | 10/2006 | Cox et al. ......................... 706/21 |
| 7,168,807 B2 | 1/2007 | Chernyak et al. |
| 7,175,278 B2 * | 2/2007 | Chernyak et al. ............. 351/246 |
| 7,261,412 B2 | 8/2007 | Somani et al. |
| 7,293,873 B2 | 11/2007 | Dai et al. |
| 7,320,517 B2 | 1/2008 | Dai et al. |
| 7,331,674 B2 | 2/2008 | Dai |
| 7,387,387 B2 | 6/2008 | Dai |
| 7,413,566 B2 | 8/2008 | Yee |
| 7,434,936 B2 | 10/2008 | Dai et al. |
| 7,475,986 B2 | 1/2009 | Dai et al. |
| 7,478,907 B2 | 1/2009 | Somani et al. |
| 2002/0099362 A1 | 7/2002 | Hohla |
| 2004/0054356 A1 | 3/2004 | Odrich et al. |
| 2005/0107775 A1 | 5/2005 | Huang et al. |

(Continued)

OTHER PUBLICATIONS

U.S. Appl. No. 08/468,898, filed Jun. 6, 2005.

*Primary Examiner* — Victor Nguyen
(74) *Attorney, Agent, or Firm* — AMO Development LLC.

(57) ABSTRACT

Systems and methods related to corneal ablation for treatment of one or more high-order optical aberrations are provided. A method includes providing a defect-correcting prescription, determining an ablation profile to impose the prescription on the cornea, and determining a sequence of laser-energy ablations to impose the ablation profile on the cornea. The prescription comprises a high-order optical correction. The ablation profile includes a first-segment profile and a second-segment profile. The second-segment profile corresponds to at least one high-order optical correction. The ablation sequence includes applying ablations corresponding to the first-segment profile prior to applying ablations corresponding to the second-segment profile.

20 Claims, 8 Drawing Sheets

(56) References Cited

U.S. PATENT DOCUMENTS

| | | |
|---|---|---|
| 2005/0261752 A1 | 11/2005 | Chernyak |
| 2007/0002274 A1 | 1/2007 | Somani et al. |
| 2008/0291395 A1 | 11/2008 | Dai |
| 2009/0000628 A1 | 1/2009 | Somani et al. |
| 2009/0036981 A1 | 2/2009 | Yee |

* cited by examiner

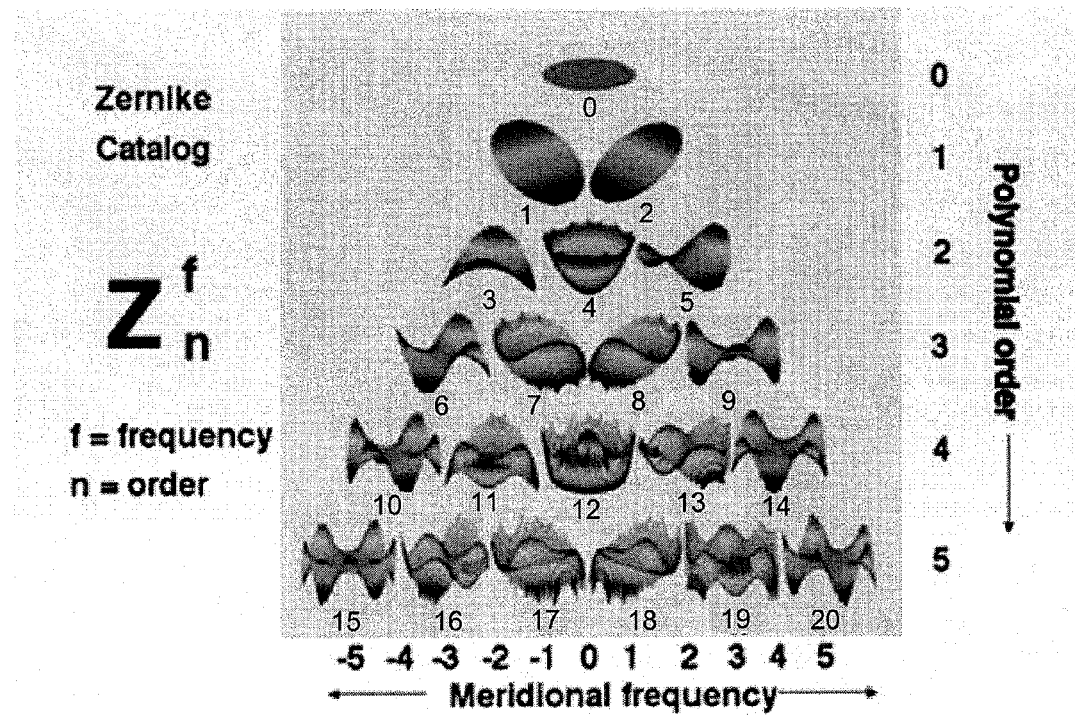

Even Zernike polynomials:
$$Z_n^m(\rho,\theta) = R_n^m(\rho)\cos(m\theta)$$
Odd Zernike polynomials:
$$Z_n^{-m}(\rho,\theta) = R_n^m(\rho)\sin(m\theta)$$

where:
$m$ and $n$ are nonnegative integers with $n \geq m$, $\theta$ is the azimuthal angle in radians, $\rho$ is the normalized radial distance, and $$R_n^m(\rho) = \sum_{k=0}^{(n-m)/2} \frac{(-1)^k (n-k)!}{k!((n+m)/2-k)!((n-m)/2-k)!}\rho^{n-2k} \quad \text{(if n-m is even)}$$

$$R_n^m(\rho) = 0 \quad \text{(if n-m is odd)}$$

FIG. 4

HIGH-ORDER OPTICAL CORRECTION DURING CORNEAL LASER SURGERY

CROSS-REFERENCE TO RELATED APPLICATION

The present invention claims the benefit of priority under 35 U.S.C. §119(e) of U.S. Provisional Application No. 61/125,209, filed Apr. 22, 2008, the entire content of which is incorporated herein by reference.

BACKGROUND

The present invention generally relates to correcting optical errors of optical systems. More particularly, the present invention relates to improved methods and systems for planning and performing a sequence of corneal alterations in a laser surgery procedure for the correction of optical errors of eyes, wherein alterations associated with the correction of high-order optical aberrations are performed during latter stages of the procedure. The methods and systems of the present invention may be particularly well-suited for planning the treatment of eyes during in situ keratomileusis (LASIK), photorefractive keratectomy (PRK), intrastromal reshaping of the cornea, and the like.

Many known laser eye surgery procedures employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photo chemically, directly breaking the intermolecular bonds.

Laser surgery procedures can be used to alter the cornea for varying purposes, such as for correcting myopia, hyperopia, astigmatism, and the like. Control over the distribution of laser energy can be provided by a variety of systems and methods, including the use of ablative masks, fixed and moveable apertures, controlled scanning systems, eye movement tracking mechanisms, and the like. In known systems, the laser beam often comprises a series of discrete pulses of laser light energy, with the total shape and amount of tissue impacted being determined by the shape, size, location, and number of laser-energy pulses impinging on the cornea. A variety of algorithms may be used to calculate the pattern of laser pulses used to alter the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements are desirable. Toward that end, wavefront measurement systems are now available to accurately measure the refractive characteristics of a particular patient's eye. One exemplary wavefront technology system is the VISX WaveScan® System, which uses a Hartmann-Shack wavefront lenslet array that can quantify aberrations throughout the entire optical system of the patient's eye, including first- and second-order sphero-cylindrical errors, coma, and third and fourth-order aberrations related to coma, astigmatism, and spherical aberrations.

Wavefront measurement of the eye can be used to create an aberration map or wavefront elevation map that permits assessment of aberrations throughout the optical pathway of the eye, e.g., both corneal and non-corneal aberrations. Creation of the wavefront elevation map involves the determination of a surface that has gradients matching the gradients measured by the wavefront sensor array. The wavefront elevation map may then be used to compute a custom defect-correcting prescription for a surgical laser system to impose so as to treat (e.g., correct, alleviate, etc.) the complex aberrations of an eye. Known methods for creating a wavefront elevation map from measured wavefront data generally involve mathematically modeling using expansion series techniques. More specifically, Zernike polynomials have been employed to model the wavefront elevation map surface. Coefficients of the Zernike polynomials are derived through known fitting techniques. Alternatively, the wavefront elevation map may be created from measured wavefront data by direct integration techniques, as described by U.S. Pat. Nos. 7,168,807 and 7,175,278, the full disclosures of which are incorporated herein by reference.

Because of the complexity of high-order aberrations, they may be difficult to correct by using traditional means such as glasses or contact lenses or by conventional refractive surgery methods. However, in at least some instances, it may be possible to use customized laser eye surgery tailored to the particular combination of aberrations present in an eye to treat high-order aberrations.

In practice, the correction of high-order aberrations may result in under correction. Accordingly, it is desirable to provide optical treatments having increased effectiveness at treating high-order aberrations.

BRIEF SUMMARY

In many embodiments, methods and systems for sequencing an alteration of a cornea so that correction of one or more high-order optical aberrations is enhanced are provided. In many embodiments, alterations associated with the treatment of at least one high-order optical aberration is performed at or near the end of a laser eye surgery procedure. By performing alterations associated with one or more high-order aberrations at or near the end of the procedure, the ability to impose one or more high-order optical corrections may be enhanced.

In a first aspect, a method for sequencing an ablation of a cornea of an eye to impose a defect-correcting prescription on the eye is provided. The method comprises providing the defect-correcting prescription, determining an ablation profile to impose the prescription on the cornea, and determining a sequence of laser-energy ablations to impose the ablation profile on the cornea. The ablation profile comprises a first-segment profile and a second-segment profile. The second-segment profile corresponds to at least one high-order optical correction. The determined sequence comprises applying ablations corresponding to the first-segment profile prior to applying ablations corresponding to the second-segment profile.

In many embodiments, the above discussed method for sequencing an ablation of a cornea to impose a defect-correcting prescription on the eye comprises one or more additional steps and/or variations. For example, the method can further comprise displaying the first-segment profile, displaying the second-segment profile, and/or displaying a predicted final cornea profile. Determining the sequence of laser-energy ablations can comprise placing ablations corresponding to the second-segment profile at the end of the sequence. The second-segment profile can be characterized using Zernike polynomials. The method can further comprise providing a wavefront elevation map of optical aberrations of the eye and determining the defect-correcting prescription in response to the wavefront elevation map. Determining the defect-correcting prescription can comprise determining a first plurality of wavefront Zernike coefficients corresponding to the wavefront map and selecting a second plurality of wavefront Zernike coefficients corresponding to the defect-correcting prescription.

In another aspect, a system for imposing a defect-correcting prescription on an eye having a cornea is provided. The system comprises a wavefront system configured to measure optical aberrations of the eye, a processor coupled with the wavefront system, and an eye-modifying assembly coupled with the processor. The processor comprises a tangible medium comprising instructions that when executed cause the processor to process the measured aberrations to generate the defect-correcting prescription for the eye, determine an ablation profile corresponding to the defect-correcting prescription, segment the ablation profile into at least a first-segment profile and a second-segment profile, and determine a sequence of laser-energy ablations to impose the ablation profile on the cornea. The second-segment profile corresponds to ablations for imposing at least one high-order optical correction on the cornea. The determined sequence comprises applying ablations corresponding to first-segment profile prior to applying ablations corresponding to the second-segment profile. The eye-modifying assembly comprises an ablative laser for directing the determined sequence of laser energy toward the cornea so as to impose the ablation profile on the cornea.

In many embodiments, the above discussed system for imposing a defect-correcting prescription on an eye having a cornea comprises one or more additional components and/or additional functionality. Additional components can include a display coupled with the processor. Additional functionality can include: a) displaying the first-segment profile and/or the second-segment profile; b) applying ablations corresponding to the second-segment profile at the end of the ablation sequence; c) displaying a predicted final cornea profile; and d) characterizing the second-segment profile using Zernike polynomials.

In another aspect, a method for treating optical aberrations of an eye having a cornea is provided. The method comprises providing a first plurality of wavefront Zernike coefficients defining a defect-correcting prescription for the eye, segmenting the first plurality of coefficients into at least a first subset and a second subset, determining a first ablation profile corresponding to the first subset, determining a second ablation profile corresponding to the second subset, determining a sequence of laser-energy ablations of the cornea, and reshaping the cornea by directing the determined sequence of laser energy toward the cornea so as to impose the defect-correcting prescription. The second subset comprises a high-order coefficient. The determined sequence comprises applying ablations corresponding to the first ablation profile prior to applying ablations corresponding to the second ablation profile.

In many embodiments, the above discussed method for treating optical aberrations of an eye having a cornea comprises one or more additional steps and/or variations. For example, the method can further comprise generating a wavefront elevation map of optical aberrations of the eye; generating a second plurality of wavefront Zernike coefficients approximating the wavefront elevation map; and determining the first plurality of coefficients in response to the second plurality of coefficients. The method can further comprise displaying at least one of the first ablation profile or the second ablation profile. Ablations corresponding to the second ablation profile can be applied at the end of the sequence. The method can further comprise displaying a predicted final cornea profile.

In another aspect, a system for imposing a defect-correcting prescription on an eye having a cornea is provided. The system comprises an aberrometer system configured to measure optical aberrations of the eye, a processor coupled with the aberrometer system, and an eye-modifying assembly coupled with the processor. The processor comprises a tangible medium comprising instructions that when executed cause the processor to process the measured aberrations to generate the defect-correcting prescription for the eye, determine a profile corresponding to the defect-correcting prescription, segment the profile into at least a first-segment profile and a second-segment profile, and determine a sequence of laser-energy to impose the profile on the cornea. The second-segment profile corresponds to laser alterations for imposing at least one high-order optical correction on the cornea. The determined sequence comprises applying alterations corresponding to first-segment profile prior to applying alterations corresponding to the second-segment profile. The eye-modifying assembly comprises a laser for directing the determined sequence of laser energy toward the cornea so as to impose the profile on the cornea.

For a fuller understanding of the nature and advantages of the present invention, reference should be made to the ensuing detailed description and accompanying drawings. Other aspects, objects, and advantages of the invention will be apparent from the drawings and detailed description that follows.

BRIEF DESCRIPTION OF THE DRAWINGS

FIG. 4 illustrates Zernike polynomial shapes and functional relationships.

DETAILED DESCRIPTION OF THE INVENTION

In many embodiments, systems, software, and methods for altering a cornea in a selected sequence are provided that accomplish alterations associated with high-order aberrations at or near the end of a laser eye surgery procedure, which may increase the effectiveness of correcting one or more high-order optical aberrations. By performing alterations associated with one or more high-order aberrations at or near the end of the procedure, the ability to induce one or more high-order optical corrections may be enhanced, which, in at least some instances, may help to reduce under correction.

In many embodiments, the disclosed systems and methods may enhance the accuracy and efficacy of laser eye surgical procedures, such as photorefractive keratectomy (PRK), phototherapeutic keratectomy (PTK), laser in situ keratomileusis (LASIK), intrastromal reshaping of the cornea (e.g., via an intrastromally focused laser, for example, a femtosecond laser), and the like. The disclosed systems and methods may produce enhanced optical accuracy by providing an improved ability to impose one or more high-order optical corrections. In many embodiments, the disclosed systems and methods employ an eye-modifying assembly comprising a laser for applying alterations to the cornea to impose a defect-correcting prescription on a pathological eye. In many embodiments, the defect-correcting prescription comprises at least one high-order optical correction. In many embodiments, the defect-correcting prescription can be identified in response to measured optical aberrations of an eye. In many embodiments, an aberrometer system, for example, a wavefront measurement system, can be used to measure the optical aberrations of an eye.

In many embodiments, the disclosed systems and methods can be readily adapted for use with existing laser systems, aberrometer systems (e.g., wavefront measurement systems), and other optical measurement devices. In many embodiments, a defect-correcting prescription can be imposed on a cornea of an eye by altering a cornea so that the treated eye regularly exceeds a 20/20 vision threshold.

While embodiments are described primarily in the context of a laser eye surgery system, it should be understood the disclosed systems and methods may be adapted for use in alternative eye treatment procedures and systems such as spectacle lenses, intraocular lenses, contact lenses, corneal ring implants, collagenous corneal tissue thermal remodeling, and the like.

Figure 1:
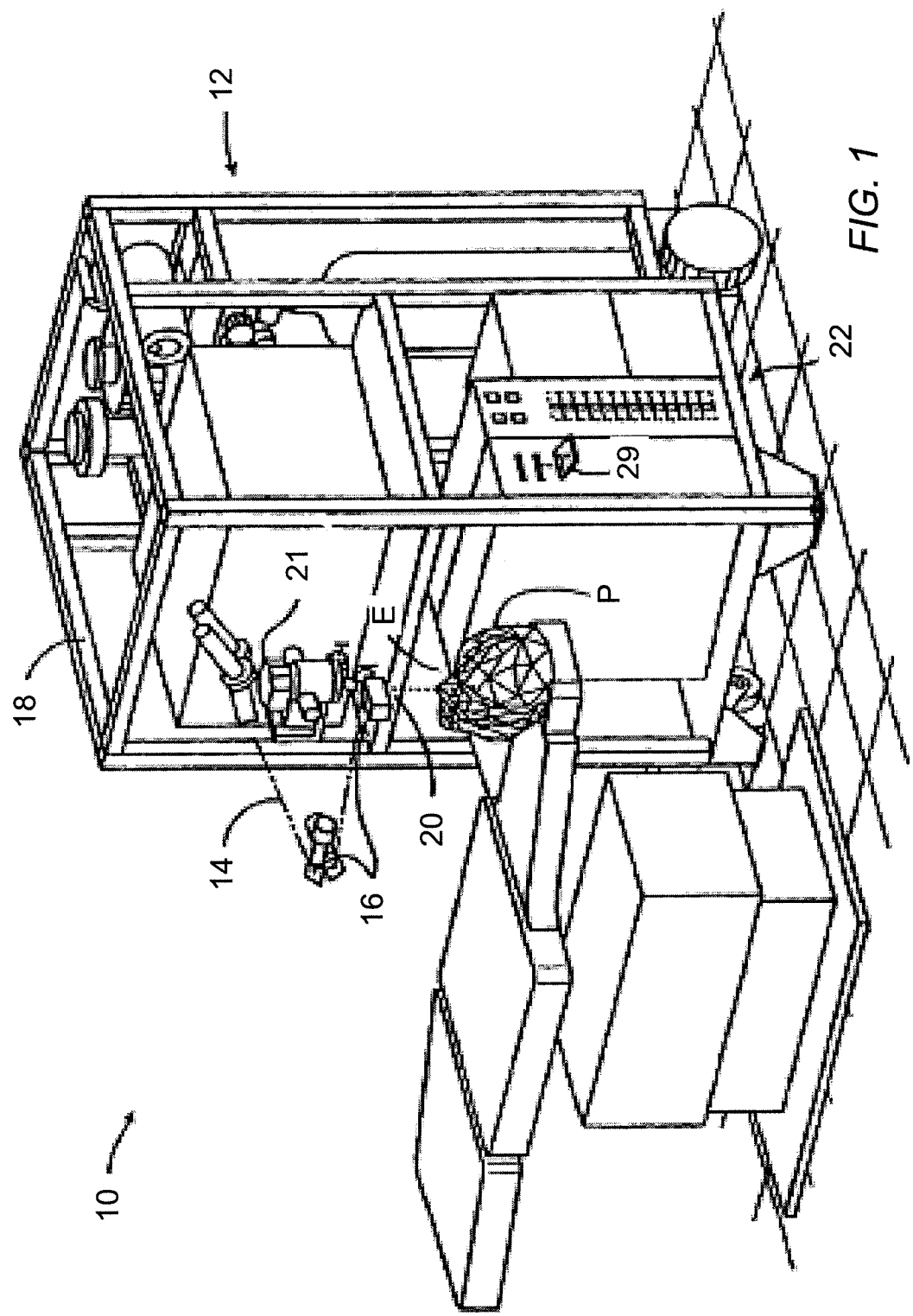
FIG. 1 is a perspective view of a laser eye surgery system in accordance with many embodiments.

Referring now to FIG. 1, a laser eye surgery system 10 in accordance with many embodiments is shown. The laser eye surgery system 10 includes a laser 12 that produces a laser beam 14. The laser 12 is optically coupled to laser-delivery optics 16, which directs the laser beam 14 to an eye E of a patient P. A delivery optics support structure (not shown here for clarity) extends from a frame 18 supporting the laser 12. A microscope 20 is mounted on the delivery optics support structure. The microscope can be used to image a cornea of the eye.

The laser 12 and the laser-delivery optics 16 will generally direct the laser beam 14 to the eye E of patient P under the direction of a computer system 22. In many embodiments, the computer system 22 will often selectively adjust the laser beam 14 to expose portions of the cornea to pulses of laser energy so as to effect a predetermined alteration of the cornea so as to alter the refractive characteristics of the eye.

In many embodiments, predetermined alterations of the cornea are sequenced so that alterations associated with imposing one or more high-order corrections are accomplished after the alterations associated with imposing other corrections, for example, low-order corrections. By performing the alterations associated with imposing one or more high-order corrections (e.g., one or more high-order corrections imposed to treat one or more high-order optical aberrations of the eye) at or near the end of the procedure, the ability to achieve locally-complex configurations in a modified cornea may be enhanced. Such locally-complex configurations may, in many embodiments, be used to impose one or more high-order optical corrections, for example, when the one or more high-order optical corrections are imposed to treat high-order optical aberrations that are not associated with the cornea.

In many embodiments, both the laser 12 and the laser delivery optical system 16 will be under control of the computer system 22 to effect the desired alteration process, with the computer system effecting (and optionally modifying) the pattern of laser pulses. The pattern of pulses may be summarized in machine-readable data of a tangible media 29 in the form of a treatment table, and the treatment table may be adjusted according to feedback input into the computer system 22 from an automated image-analysis system (or manually input into the processor by a system operator) in response to real-time feedback data provided from a monitoring feedback system. The laser treatment system 10, which comprises the computer system 22, may continue and/or terminate a treatment in response to the feedback, and may optionally also modify the planned treatment based at least in part on the feedback.

In many embodiments, the laser 12 comprises an excimer laser, for example, an argon-fluorine laser producing pulses of laser light having a wavelength of approximately 193 nm. In many embodiments, the laser 12 is configured to provide a feedback-stabilized fluence at the patient's eye, delivered via the laser-delivery optics 16. In many embodiments, alternate sources of laser energy may be used, for example, alternate sources of ultraviolet or infrared radiation, for example, those adapted to controllably ablate corneal tissue or alter the cornea without causing significant damage to adjacent and/or underlying tissues of the eye. Although an excimer laser is an illustrative source of a laser beam in many embodiments disclosed herein, in many embodiments, other lasers, including those known in the art, may be used to ablate or otherwise alter the cornea.

Additional components and subsystems may be included with the laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system can also be used.

Figure 2:
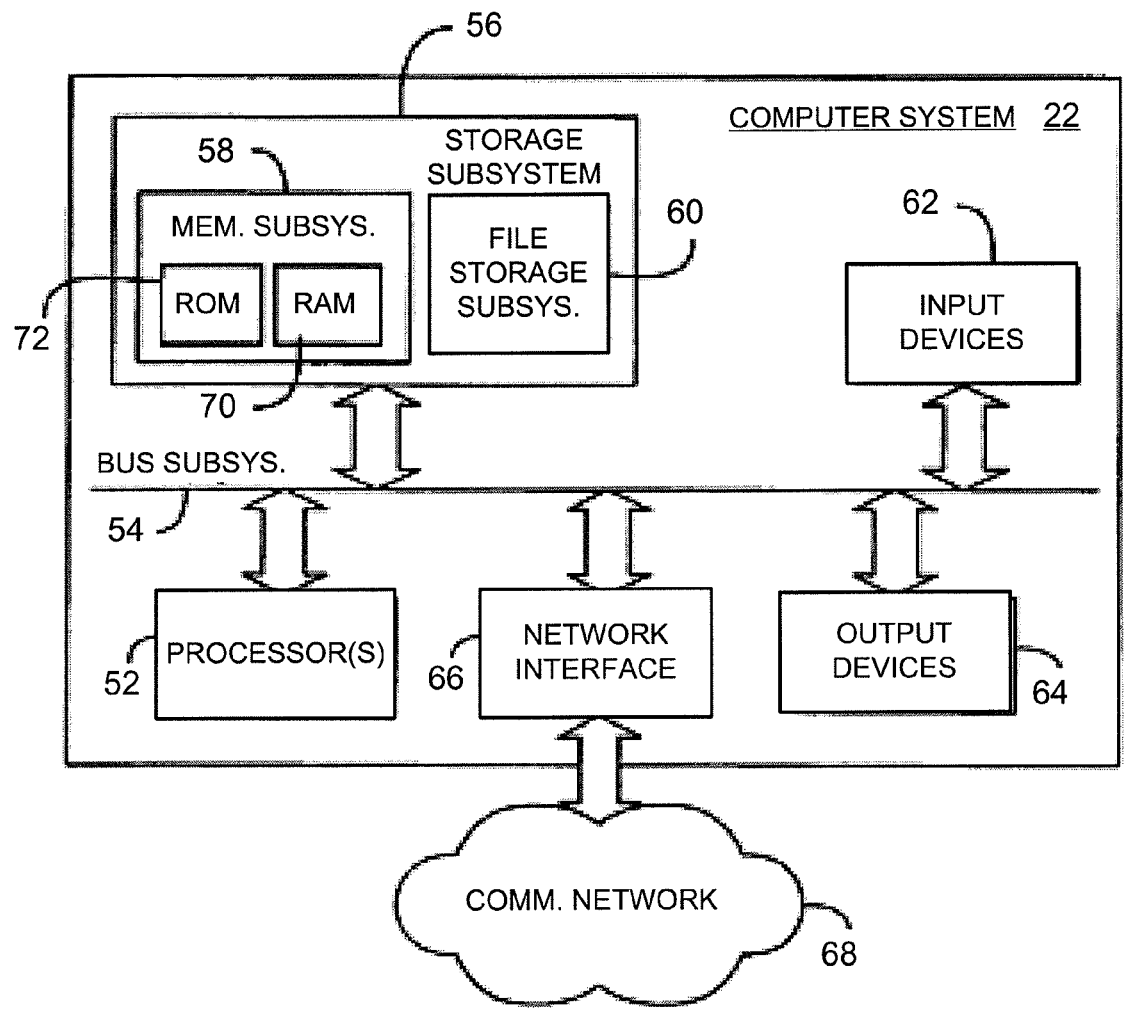
FIG. 2 diagrammatically illustrates a computer system in accordance with many embodiments.

FIG. 2 is a simplified block diagram of an example computer system 22 that may be used by the laser surgical system 10 in accordance with many embodiments. The computer system 22 typically includes at least one processor 52, which may communicate with a number of peripheral devices via a bus subsystem 54. In many embodiments, these peripheral devices include a storage subsystem 56, comprising a memory subsystem 58 and a file storage subsystem 60; user-interface input devices 62; user-interface output devices 64; and a network interface subsystem 66. The network interface subsystem 66 provides an interface to outside networks 68 and/or other devices, such as a wavefront measurement system 30 (shown in FIG. 3A).

In many embodiments, the user-interface input devices 62 can include any of a wide variety of known input devices (e.g., a keyboard; a pointing devices such as a mouse, a trackball, a touch pad, or graphics tablet; a scanner, one or more foot pedals, a joystick, a touch screen incorporated into the display, audio input devices such as voice recognition systems, microphones, and other types of input devices). In many embodiments, user input devices 62 can be used to download a computer-executable code from the tangible storage media 29 embodying any of the methods disclosed herein. In general, use of the term "input device" is intended to include a variety of conventional and proprietary devices and ways to input information into the computer system 22.

In many embodiments, the user-interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from the computer system 22 to a user.

In many embodiments, the storage subsystem 56 stores the basic programming and data constructs that provide the functionality of the embodiments. For example, in many embodiments, a database and modules implementing the functionality of the methods, as described herein, may be stored in the storage subsystem 56. In many embodiments, these software modules are executed by the processor(s) 52. In a distributed environment, the software modules may be stored on a plurality of computer systems and executed by processors of the plurality of computer systems. In many embodiments, the storage subsystem 56 comprises the memory subsystem 58 and the file storage subsystem 60.

In many embodiments, the memory subsystem 58 includes a number of memories, for example, a main random-access memory (RAM) 70 for storage of instructions and data during program execution and a read-only memory (ROM) 72 in which fixed instructions are stored. In many embodiments, the file storage subsystem 60 provides persistent (non-volatile) storage for program and data files, and may include the tangible storage media 29 (shown in FIG. 1) which may optionally embody wavefront sensor data, wavefront gradients, a wavefront elevation map, a treatment map, and/or a laser treatment table. The file storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other computers coupled with the computer system 22. The modules implementing the functionality in many embodiments may be stored by the file storage subsystem 60.

The bus subsystem 54 provides a mechanism for letting the various components and subsystems of the computer system 22 communicate with each other as intended. The various subsystems and components of the computer system 22 need not be at the same physical location but may be distributed at various locations within a distributed network. Although the bus subsystem 54 is shown schematically as a single bus, alternate embodiments of the bus subsystem may utilize multiple busses.

The computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of the computer system 22 depicted in FIG. 2 is intended only as a specific example for purposes of illustrating embodiments of the present invention. Many other configurations of the computer system 22 are possible having more or less components than the computer system depicted in FIG. 2.

In many embodiments, an aberrometer system, for example, a wavefront measurement system, is used to assess the optical aberrations that exist in an eye. Wavefront measurement systems work by measuring the way a wavefront of light passes through the various refractive or focusing components of the eye, such as the cornea and crystalline lens. In one approach, a narrow beam of light is directed upon the retina of an eye and its reflection emerges from the eye. In the case of an ideal eye, the emerging reflection is comprised of uniformly parallel beams of light. However, in the case of a non-ideal eye, the emerging reflection is comprised of non-parallel beams of light due to various optical aberrations throughout the eye. Some wavefront measurements systems use an array of lenses and associated sensors to provide a collection of measurements or gradients, each gradient indicating how much a particular region of the emerging reflection deviates from the ideal parallel path. The measured gradients can then be used to determine a wavefront elevation map having the same gradients as the measured gradients. The wavefront elevation map is a graphical representation of the optical aberrations in the eye, and, with regard to corneal alteration via ablation of the anterior surface of the cornea, is closely correlated with the ablation profile that must be removed to correct the optical aberrations.

Figure 3A:
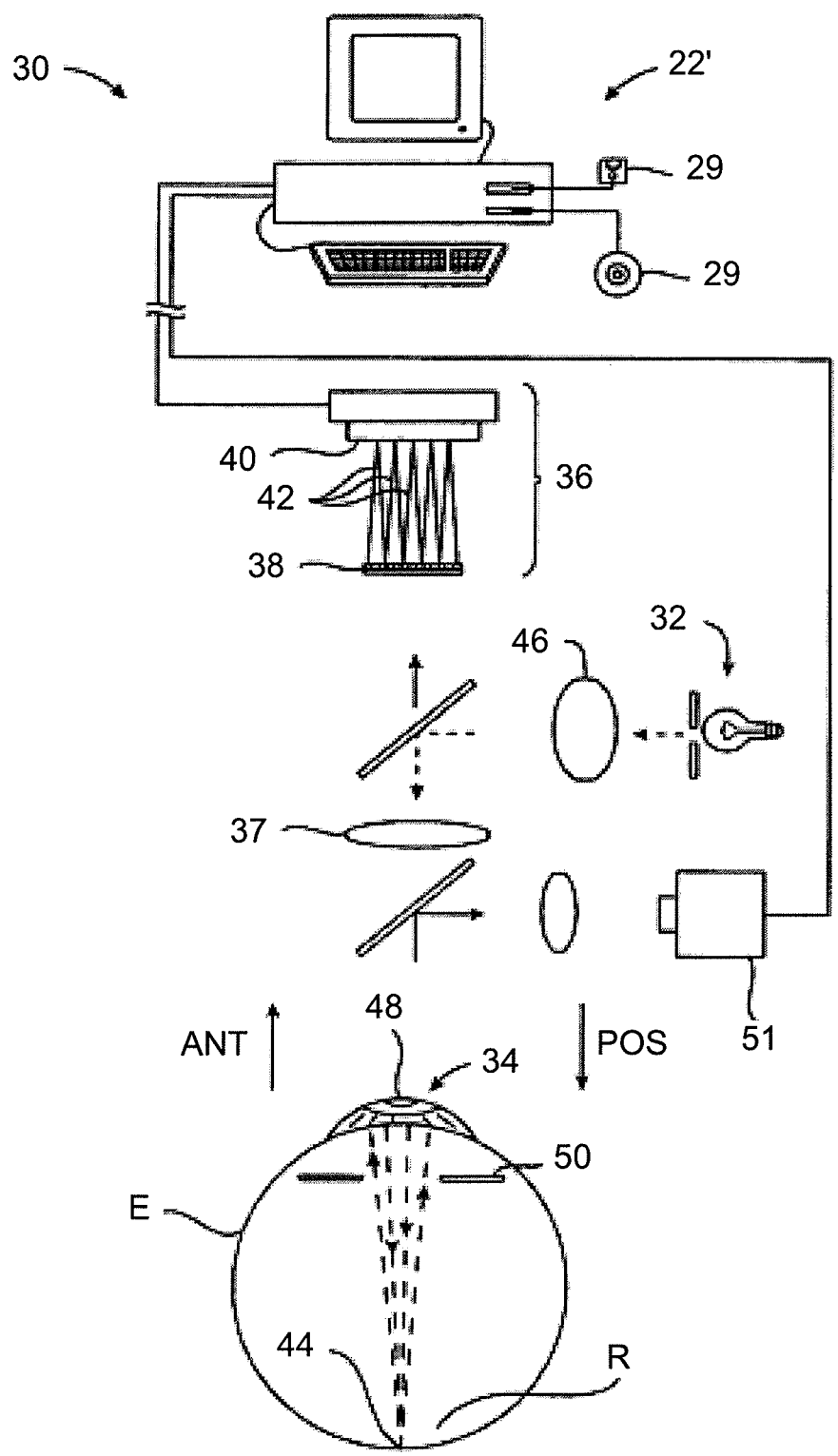
FIG. 3A illustrates a wavefront measurement system in accordance with many embodiments.

Referring now to FIG. 3A, one embodiment of a wavefront measurement system 30 is schematically illustrated in simplified form. In very general terms, the wavefront measurement system 30 is configured to sense local slopes of light exiting the patient's eye. Devices based on the Hartmann-Shack principle generally include a lenslet array to sample light uniformly over an aperture, which is typically the exit pupil of the eye. Thereafter, the local slopes of the exiting light are analyzed so as to reconstruct the wavefront surface or map.

More specifically, the wavefront measurement system 30 includes an image source 32, such as a laser, which projects a source image through optical tissues 34 of an eye E so as to form an image 44 upon a surface of a retina R. The image from the retina R is transmitted by the optical system of the eye (e.g., the optical tissues 34) and imaged onto a wavefront sensor 36 by system optics 37. The wavefront sensor 36 communicates signals to a computer system 22' for measurement of the optical errors in the optical tissues 34 and, in many embodiments, determination of a defect-correcting prescription. The computer 22' may include the same or similar hardware as the computer system 22 illustrated in FIGS. 1 and 2. The computer system 22' may be in communication with the computer system 22 that directs the laser surgery system 10, or some or all of the components of the computer system 22, 22' of the wavefront measurement system 30 and the laser surgery system 10 may be combined or separate. If desired, data from the wavefront sensor 36 may be transmitted to the laser computer system 22 via the tangible media 29, via an I/O port, via an networking connection 66 such as an intranet or the Internet, or the like.

The wavefront sensor 36 generally comprises a lenslet array 38 and an image sensor 40. As the image from the retina R is transmitted through the optical tissues 34 and imaged onto the wavefront sensor 36, the lenslet array 38 separates the transmitted image into an array of beamlets 42, and (in combination with other optical components of the system) images the separated beamlets 42 on the surface of the sensor 40. The sensor 40 typically comprises a charged coupled device ("CCD") and senses characteristics of these individual beamlets, which can be used to determine the characteristics of an associated region of the optical tissues 34. In particular, where the image 44 comprises a point or small spot of light, a location of a transmitted spot as imaged by a beamlet can directly indicate a local gradient of the light transmitted through the associated region of the optical tissue.

The eye E generally defines an anterior orientation ANT and a posterior orientation POS. The image source 32 generally projects an image in a posterior direction through the optical tissues 34 onto the retina R as indicated in FIG. 3A. The optical tissues 34 transmit the image 44 from the retina in the anterior direction toward the wavefront sensor 36. The image 44 transmitted through the optical tissues 34 may be distorted by any imperfections in the eye's optical system. Optionally, image source projection optics 46 may be configured or adapted to decrease any distortion of image 44.

In some embodiments, the image source optics 46 may decrease low-order optical errors by compensating for spherical and/or cylindrical errors of the optical tissues 34. High-order optical errors of the optical tissues may also be compensated through the use of an adaptive optic element, such as a deformable mirror (described below). Use of an image source 32 selected to define a point or small spot as the image 44 upon the retina R may facilitate the analysis of the data provided by the wavefront sensor 36. Distortion of the image 44 may be limited by transmitting a source image through a central region 48 of the optical tissues 34, which is smaller than a pupil 50, as the central portion of the optical tissues may be less prone to optical errors than a peripheral portion. Regardless of the particular image source structure, it will be generally be beneficial to have a well-defined and accurately formed image 44 on the retina R.

In some embodiments, the measured wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3A) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of many embodiments will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from the pupil camera 51. In many embodiments, the pupil camera 51 images the pupil 50 so as to determine a position of the pupil for registration of the wavefront sensor data relative to the optical tissues.

Figure 3B:
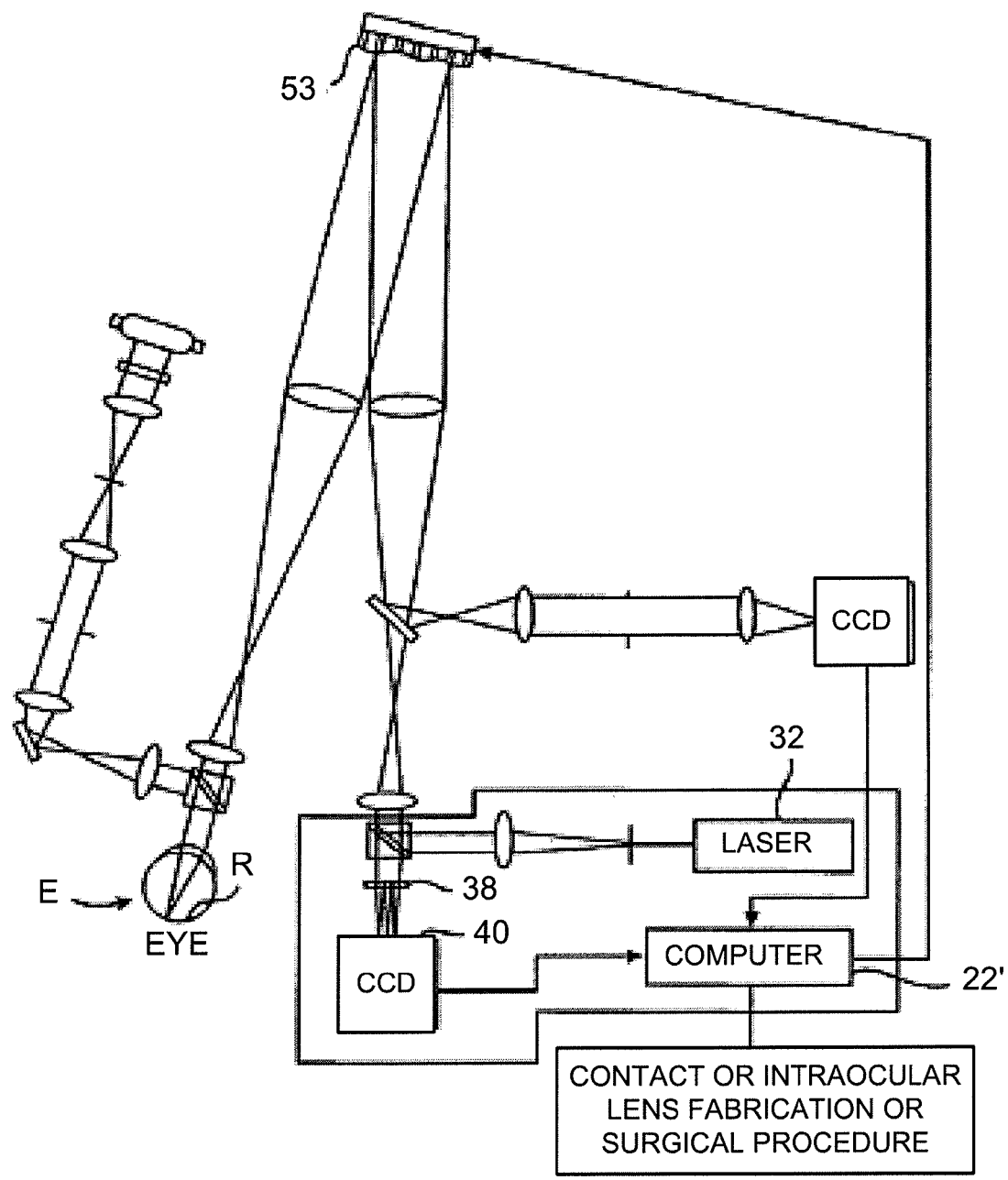
FIG. 3B illustrates another wavefront measurement system in accordance with many embodiments.

An alternative embodiment of a wavefront measurement system is illustrated in FIG. 3B. The major components of the system of FIG. 3B are similar to those of FIG. 3A. Additionally, FIG. 3B includes an adaptive optical element 53 in the form of a deformable mirror. The source image is reflected from the deformable mirror 53 during transmission to the retina R, and the deformable mirror is also along the optical path used to form the transmitted image between the retina R and the imaging sensor 40. The deformable mirror 53 can be controllably deformed by the computer system 22' to limit distortion of the image formed on the retina or of subsequent images formed of the images formed on the retina, and may enhance the accuracy of the resultant wavefront data. The structure and use of the system of FIG. 3B are more fully described in U.S. Pat. No. 6,095,651, the full disclosure of which is incorporated herein by reference.

In many embodiments, the components of a wavefront measurement system for measuring the eye comprise elements of a VISX WaveScan®, available from VISX, Incorporated of Santa Clara, Calif. In many embodiments, a wavefront measurement system includes a WaveScan® with a deformable mirror as described above. An alternate embodiment of a wavefront measuring system is described in U.S. Pat. No. 6,271,915, the full disclosure of which is incorporated herein by reference.

Although a wavefront elevation map may be created from optical gradient data in any number of ways, wavefront elevation map creation by way of fitting the gradient data to a combination of one or more Zernike polynomials is one commonly used approach. Zernike polynomials represent a particularly beneficial form of a mathematical series expansion for modeling the wavefront elevation map. FIG. 4 illustrates the shapes of a subset of Zernike polynomials and provides the Zernike functional relationships, which are a function of normalized radius and angle for a given order and frequency. In many embodiments, Zernike polynomial sets including terms 0 through 6th order or 0 through 10th order are used. The coefficients $a_n$ for each Zernike polynomial $Z_n$ may, for example, be determined using a standard least-squares fit technique. In practice, the number of Zernike polynomial coefficients used may be limited (for example, to about 28 coefficients).

Where an array of Zernike coefficients has been determined, the wavefront elevation map can be created. Scaling the Zernike polynomials by their coefficients and summing the scaled Zernike polynomials allows a wavefront elevation map to be calculated, and in some cases, may very accurately reconstruct a wavefront elevation map.

An additional benefit to wavefront elevation reconstruction by way of Zernike polynomials relates to the correspondence between certain Zernike polynomial shapes and commonly known optical aberrations, such as between Zernike polynomial for defocus (n=2, f=0) and nearsightedness or farsightedness, as well as the Zernike polynomial shapes for astigmatism (n=2, f=±2). The low-order aberrations of defocus and astigmatism account for a vast majority of the optical errors present in a typical eye.

However, high-order aberrations corresponding to high-order Zernike polynomials do exist to a significant extent, and are associated with vision errors such as difficulty seeing at night, glare, halos, blurring, starburst patterns, double vision, or the like. Accordingly, improved vision correction may result by way of improved correction of high-order aberrations.

Figure 5:
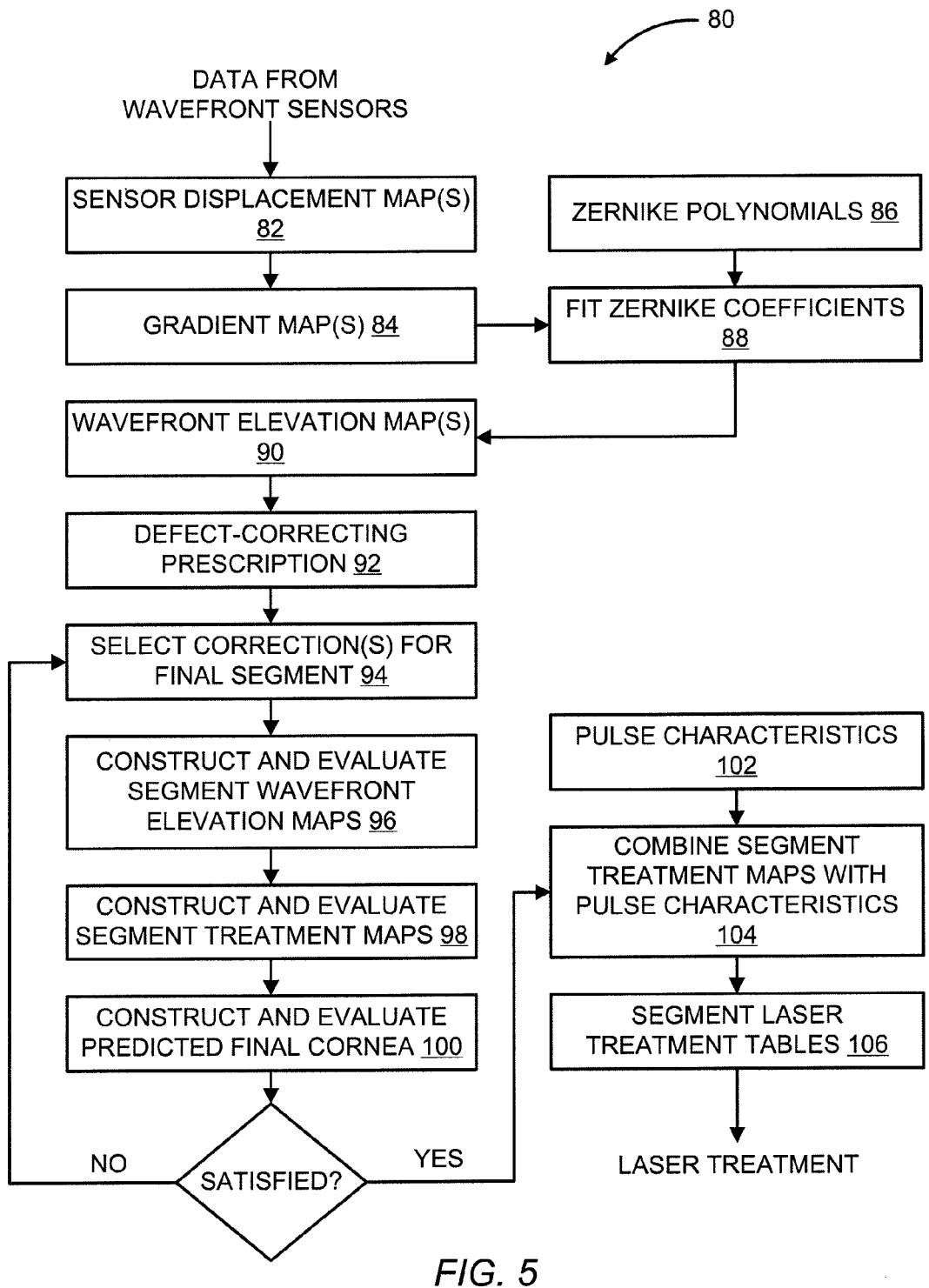
FIG. 5 is a flow chart that schematically illustrates a method of determining a sequence of a corneal alterations in accordance with many embodiments.

Turning now to FIG. 5, a method 80, in accordance with many embodiments, for determining a laser alteration of a cornea is illustrated. As can be appreciated, the illustrated method should not be limited to the order of steps, or the specific steps illustrated, and various modifications to the method, such as having more or less steps, may be made. The illustrated method can be carried out by a system that includes a processor and a memory coupled to the processor. The memory can be configured to store a plurality of modules which have the instructions and algorithms for carrying out the steps of the method.

A wavefront measurement system that includes a wavefront sensor (for example, a Hartmann-Shack sensor) can be used to obtain one or more sensor displacement maps (e.g., Hartmann-Shack displacement maps) of the optical tissues of an eye. The sensor displacement map 82 can be obtained by transmitting an image through the optical tissues of the eye and sensing the exiting wavefront surface. As described above, the data from the wavefront sensors can be generated by shining a small spot or point of light onto the retina, which produces reflected light which then exits the eye and is captured by the wavefront sensors. The data from the wavefront sensors can be used to produce an array of optical gradients or a gradient map 84. The optical gradient data can then used to create an optical surface or a wavefront elevation map 90 by mathematically reconstructing a surface with contours consistent with the optical gradient data, such as by modeling the surface as a combination of Zernike polynomials 86, 88 as described above.

In step 92, a defect-correcting prescription is identified or provided. In many embodiments, one or more wavefront elevation maps 90 can be used to identify a defect-correcting prescription that at least partially corrects optical aberrations of the eye reflected by the one or more wavefront elevation maps 90. In many embodiments, the defect-correcting prescription can be identified by selecting two or more discrete corrections for treatment of a corresponding two or more discrete optical aberrations. The two or more discrete corrections can include one or more high-order corrections for treatment of a corresponding one or more high-order aberrations. In many embodiments, the two or more discrete corrections can be selected in response to the wavefront Zernike coefficients corresponding to one or more wavefront elevation maps.

In many embodiments, the defect-correcting prescription can be identified in alternate ways. For example, a previously identified defect-correcting prescription can be simply provided as a starting point. The defect-correcting prescription can also be identified using methods described in numerous patents, patent publications, and patent applications assigned to Advanced Medical Optics, Inc., including, for example, U.S. Pat. Nos. 6,280,435; 6,663,619; 7,261,412; 7,293,873; 7,320,517; 7,387,387; 7,413,566; 7,434,936; 7,475,986; 7,478,907; and U.S. Pat. Publication Nos. 2004/0054356 A1; US 2005/0261752 A1; 2008/0291395 A1; 2009/0000628 A1; and 2009/0036981 A1; the entire disclosures of which are hereby incorporated by reference herein.

Once the defect-correcting prescription has been identified, one or more high-order corrections from the defect-correcting prescription are selected (step 94). The one or more high-order corrections are selected so that corresponding alterations to impose the one or more high-order corrections can be accomplished during the final stages of the laser vision correction procedure. As will be described in more detail below, reserving the correction of high-order aberration(s) until the end of the procedure may improve the ability to achieve a desired locally-complex configuration in the final cornea.

In step 96, the selected one or more high-order corrections can be used to construct and evaluate segment wavefront elevation maps corresponding to a segmented defect-correcting prescription. The segment wavefront elevation maps are analogous to the wavefront elevation map defining the measured optical aberrations of an eye, but differ in that the segment wavefront elevation maps define the optical corrections selected for imposition upon the eye during a segment of the alteration procedure. The selected high-order corrections (selected in step 94) can be used to construct one of the segment wavefront elevation maps. The selected high-order corrections can be subtracted from the defect-correcting prescription and the remaining defect correction used to define one or more of the segment wavefront elevation maps that corresponds to candidate corrections for application prior to the selected high-order corrections. Because, as discussed above, a wavefront elevation map is closely correlated with a corresponding alteration profile (at least with respect to alteration via ablation of a surface of the cornea), these wavefront elevation maps can be evaluated to gain insight into the corresponding alteration profiles. For example, these elevation maps can be evaluated to assess whether the selected segmentation of the defect-correcting prescription will likely result in corresponding alteration profile segments that impose alteration profile segments with locally-complex configurations later in the alteration sequence. Moreover, inspection of these segment wavefront elevation maps can be accomplished to provide a preview of the related segment treatment maps (constructed and evaluated in step 98) containing the definition of the targeted corneal alterations during the corresponding segments of the alteration procedure. At this point, the treating professional may decide to reallocate particular corrections to a different point in the treatment sequence, or even split a correction between segments, for example, by apportioning a particular Zernike coefficient between two or more segments.

An additional part of the creation of the segment wavefront elevation maps (step 96) can involve checking that each of the sequence of segment wavefront elevation maps will result in acceptable alteration segments. For example, in many embodiments the alteration comprises accomplishing ablation of the anterior surface of the cornea. Each of the sequence of segment wavefront elevation maps can be checked to ensure that corresponding ablation shapes do not exceed the shape of the ablation remaining to be accomplished following that segment. For example, the ablation shape that is associated with the first segment elevation map cannot locally exceed the total ablation shape to be removed. Likewise, the ablation shape for the second segment cannot locally exceed the remaining ablation shape to be removed following removal of the ablation shape associated with the first segment elevation map. Instances where the segment ablation shape locally exceeds the remaining ablation shape require appropriate adjustment to the segmentation, such as by reassigning the locally exceeding parts of the segment to later segments, or by adjusting the allocation of aberrations so as to eliminate any locally exceeding parts of the segment. Because ablation shape is closely correlated with the associated segment wavefront elevation map, this checking can be done by way of appropriate comparison between the defect-correcting prescription (from step 92) and the segment wavefront elevation maps. Analogous checking of segments can also be accomplished where the alterations are imposed by other methods.

After the segment wavefront elevation maps are created, segment treatment maps can be constructed. For example, in many embodiments comprising ablation of a surface of the cornea, the transformation between a segment wavefront elevation map and its corresponding corrective ablation shape can be viewed as being predominantly linear with the ablation shape being obtained by multiplying the wavefront elevation by $1/(n-1)$ where n is the index of refraction of the cornea of 1.377. At this point, the treating professional may decide to reallocate particular corrections to a different point in the treatment sequence, or even split a correction between segments, as can be done by apportioning a particular Zernike coefficient between two or more segments as discussed above.

Figure 6:
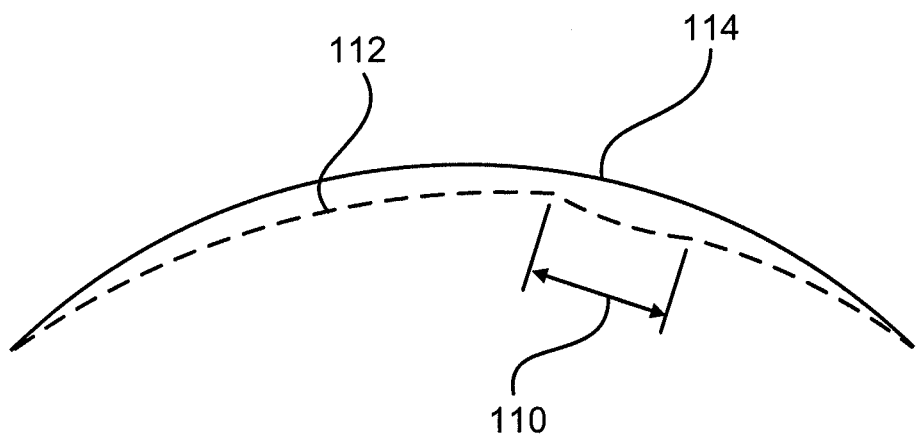
FIG. 6 diagrammatically illustrates an initial cornea profile and a final cornea profile with a local region of complex shape.

In at least some instances, for example instances involving ablation of the anterior surface of the cornea, a desired shape for the profile of the cornea remaining following laser eye surgery may not be uniformly smooth, but may instead contain regions with locally-complex shapes for treatment of high-order aberrations which are actually caused elsewhere in the ocular system, such as in the lens. Such a region of locally-complex shape 110 is depicted in FIG. 6, which illustrates a final cornea profile 112 superimposed upon a corresponding initial cornea profile 114. The difference between the initial cornea profile 114 and the final cornea profile 112 represents the depth of the material removed during an ablation procedure. The final cornea profile depicted comprises an area of locally-complex shape, the function of which is to correct a high-order aberration that may arise elsewhere in the eye, such as in the lens. Especially where the total ablation depth is significant with respect to the dimensions of the locally-complex shape, which may increase the amount of smoothing that occurs as a result of the ablation, the ability to achieve the desired locally-complex shape may be enhanced by reserving the ablation associated with the locally-complex shape until the end of the procedure.

For any particular set of aberrations to be targeted for correction, it may be helpful to further construct and evaluate a predicted final cornea (step 100 in FIG. 5). For example, in many embodiments involving ablation of the anterior surface of the cornea, by combining all of the segment treatment maps and subtracting the corresponding ablation profile from a starting shape of the cornea, a predicted final cornea profile may be obtained. Evaluation of the final cornea profile may provide useful information regarding which of one or more high-order corrections correspond with locally-complex shapes on the final cornea profile, thereby making such high-order corrections candidates for inclusion in a latter segment of the ablation procedure. Additionally, evaluation of the predicted final cornea profile may result in the inclusion or exclusion of specific corrections, or even portions of specific corrections, in the overall procedure, so as to provide the ability to balance which aberrations to correct via the defect-correcting prescription against the resulting predicted final cornea shape.

Once a satisfactory allocation of aberrations among the selected treatment segments is obtained, the process proceeds with the formulation of corresponding segment laser treatment tables (step 106). The segment laser treatment tables may include parameters for laser beam pulses, for example, positions of the laser beam relative to the eye (e.g., horizontal, vertical, and depth in the case of an intrastromally focused laser) for each laser beam pulse in a series of pulses. In many embodiments involving ablation of the anterior surface of the cornea, the diameter of the beam may be varied during the treatment, for example, from about 0.65 mm to 6.5 mm. The segment laser treatment tables may include between several hundred pulses to five thousand or more pulses, and the number of laser beam pulses may vary with the amount of material removed and/or altered and laser beam diameters employed by the segment laser treatment tables. The segment laser treatment tables may optionally be optimized by sorting of the individual pulses so as to avoid localized heating, minimize irregular ablations if the treatment program is interrupted, and the like. The eye can thereafter be altered according to the segment laser treatment tables (e.g., via ablation of the anterior surface of the cornea, via intrastromal reshaping of the cornea, etc.).

In many embodiments, the segment laser treatment tables may adjust the laser beam to produce the desired alterations using a variety of alternative mechanisms. The laser beam may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539 and 6,347,549, the full disclosures of which are incorporated herein by reference.

Still further alternatives are possible, including scanning of the laser beam over a surface of the eye and controlling the number of pulses and/or dwell time at each location, as described, for example, by U.S. Pat. No. 4,665,913 (the full disclosure of which is incorporated herein by reference); using masks in the optical path of the laser beam to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; intrastromal femtosecond reshaping of the cornea, or the like.

One example method and system for preparing segment laser treatment tables for ablation of the anterior surface of the cornea is described in U.S. Pat. No. 6,673,062, entitled "Generating Scanning Spot Locations for Laser Eye Surgery," the full disclosure of which is incorporated herein by reference.

Figure 7:
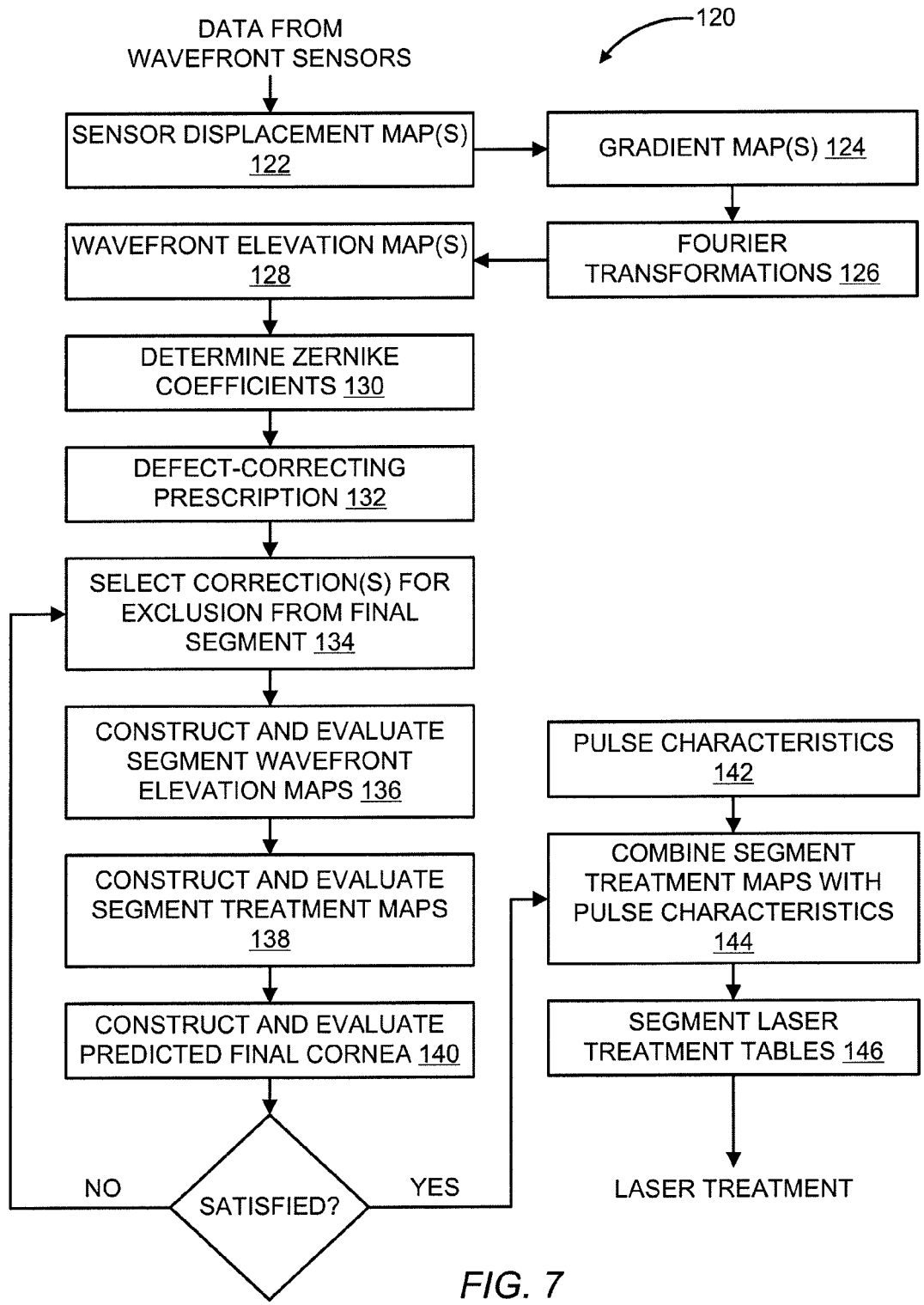
FIG. 7 is a flow chart that schematically illustrates another method of determining a sequence of a corneal alterations in accordance with many embodiments.

Turning now to FIG. 7, a method 120, in accordance with many embodiments, for determining a laser alteration of a cornea is illustrated. As illustrated, the creation of the wavefront elevation map 128 from the gradient map 124 may alternatively be accomplished by way of integration using Fourier transformations 126, as described by U.S. Pat. Nos. 7,168,807 and 7,175,278, the full disclosures of which are incorporated herein by reference. As described in the above referenced patents, construction of wavefront elevation map 128 by way of integration using Fourier transformations 126 may provide advantages of speed and/or increased accuracy as compared to reconstruction by way of fitting Zernike polynomials.

For potential use during the subsequent segmentation of the sequence of the laser treatment procedure, Zernike polynomial coefficients can be determined (step 130) by known methods, such as by least-square fitting procedures. Alternatively, where the wavefront elevation map 128 was determined by way of integration using Fourier transformations 126, the Zernike polynomial coefficients may be directly calculated from the Fourier coefficients using the methods described by U.S. Pat. No. 7,331,674, entitled "Calculating Zernike Coefficients from Fourier Coefficients," the full disclosure of which is incorporated herein by reference. The determination of Zernike polynomials may provide a convenient way to characterize constituent aberrations contributing to a particular wavefront elevation map.

Step 134 of FIG. 7 uses a different approach for the segregation of corrections than the analogous step of FIG. 5. In the process of FIG. 5, the wavefront elevation map 90 was created by a combination of discrete Zernike coefficients. While the defect-correcting prescription 92, 132 is not limited to the correction of aberrations corresponding to a combination of discrete Zernike coefficients, in many embodiments it may correspond to such a combination. As a result, the segregation process of FIG. 5 can be used in instances where one or more high-order corrections correspond to one or more discrete Zernike coefficients. In contrast, the segregation process of FIG. 7 is directed towards the segregation of a defect-correcting prescription where the one or more high-order corrections for imposition during the final segment of the alteration procedure do not necessarily correspond to one or more discrete Zernike coefficients. For example, with a defect-correcting prescription identified in response to a wavefront elevation map that is constructed via Fourier transformations, the defect-correcting prescription may contain high-order corrections that do not exactly match a combination of discrete Zernike coefficients. The segregation process of FIG. 7 can address such a situation by selecting low-order corrections for exclusion from the final segment, as opposed to the selection of high-order corrections for inclusion in the final segment, as provided for in the process of FIG. 5.

The final segment wavefront elevation map can be constructed from the defect-correcting prescription by subtracting the selected low-order corrections from the defect-correcting prescription. This approach has the advantage of including in the final segment any differential corrections that would exist between a defect-correcting prescription that is not an exact combination of discrete Zernike coefficients and a corresponding defect-correcting prescription that is an exact combination of discrete Zernike coefficients. Although the use of the above determined Zernike coefficients provides one way of separating a defect-correcting prescription into low-order and high-order corrections, alternative approaches may be used. Beyond the above described differences, the remaining process illustrated in FIG. 7 corresponds with that discussed above with reference to FIG. 5.

It is understood that the examples and embodiments described herein are for illustrative purposes and that various modifications or changes in light thereof will be suggested to persons skilled in the art and are included within the spirit and purview of this application and the scope of the appended claims. Numerous different combinations are possible, and such combinations are considered part of the present invention.

What is claimed is:

1. A method for treating optical aberrations of an eye having a cornea, the method comprising:
providing a first plurality of wavefront Zernike coefficients defining a defect-correcting prescription for the eye;
segmenting the first plurality of coefficients into at least a first subset and a second subset, the second subset comprising a high-order coefficient associated with a locally complex desired change in refractive configuration of the eye;
determining a first ablation profile corresponding to the first subset;
determining a second ablation profile corresponding to the second subset;
determining a sequence of laser-energy ablations of the cornea, wherein the sequence comprises applying ablations corresponding to the first ablation profile prior to applying ablations corresponding to the second ablation profile; and
reshaping the cornea by directing the determined sequence of laser energy toward the cornea so as to impose the defect-correcting prescription and so that the locally complex desired change in refractive configuration is imposed after, and is not smoothed by, the first ablation profile.

2. The method of claim 1, further comprising:
generating a wavefront elevation map of optical aberrations of the eye;
generating a second plurality of wavefront Zernike coefficients approximating the wavefront elevation map; and
determining the first plurality of coefficients in response to the second plurality of coefficients.

3. The method of claim 2, wherein the wavefront elevation map is generated by way of integration using Fourier transformations and the second plurality of wavefront Zernike coefficients are generated from the Fourier Coefficients.

4. The method of claim 3, wherein the first plurality of coefficients are determined in response to the second plurality of coefficients by selecting corrections for exclusion from the second ablation profile.

5. The method of claim 1, further comprising displaying at least one of the first ablation profile or the second ablation profile.

6. The method of claim 1, wherein ablations corresponding to the second ablation profile are applied at the end of the sequence.

7. The method of claim 1, further comprising displaying a predicted final cornea profile.

8. The method of claim 1, further comprising constructing and evaluating at least one wavefront elevation maps constructed from one of the first subset and the second subset of coefficients.

9. The method of claim 8, wherein the evaluating comprises ensuring that corresponding ablation profiles do not exceed a profile of the ablation remaining to be accomplished following that segment.

10. The method of claim 9, further comprising adjusting the first subset and second subset when the first ablation profile or second ablation profile locally exceeds a profile of the ablation remaining to be accomplished.

11. The method of claim 10, wherein the adjusting comprises reassigning a locally exceeding part of the first subset to the second subset.

12. The method of claim 10, wherein the adjusting comprises reallocating aberrations between the subsets so as to eliminate any locally exceeding parts of the subset.

13. The method of claim 1, further comprising constructing and evaluating at least one treatment map constructed from one of the first subset and the second subset of coefficients.

14. A method for treating optical aberrations of an eye having a cornea, the method comprising:
generating a first plurality of wavefront Zernike coefficients approximating a wavefront elevation map;
generating the wavefront elevation map of optical aberrations of the eye;
wherein the wavefront elevation map is generated by way of fitting gradient data to a combination of one or more Zernike polynomials and wherein the first plurality of wavefront Zernike coefficients are determined by a least-squares fit technique;

determining a second plurality of coefficients in response to the first plurality of coefficients, the second plurality of wavefront Zernike coefficients defining a defect-correcting prescription for the eye;

segmenting the second plurality of coefficients into at least a first subset and a second subset, the second subset comprising a high-order coefficient;

determining a first ablation profile corresponding to the first subset;

determining a second ablation profile corresponding to the second subset;

determining a sequence of laser-energy ablations of the cornea, wherein the sequence comprises applying ablations corresponding to the first ablation profile prior to applying ablations corresponding to the second ablation profile;

reshaping the cornea by directing the determined sequence of laser energy toward the cornea so as to impose the defect-correcting prescription.

15. The method of claim 14, wherein the first plurality of coefficients are determined in response to the second plurality of coefficients by selecting one or more high-order corrections to provide with the second ablation profile.

16. The method of claim 14, further comprising constructing and evaluating at least one wavefront elevation maps constructed from one of the first subset and the second subset of coefficients.

17. The method of claim 16, wherein the evaluating comprises ensuring that corresponding ablation profiles do not exceed a profile of the ablation remaining to be accomplished following that segment.

18. The method of claim 17, further comprising adjusting the first subset and second subset when the first ablation profile or second ablation profile locally exceeds a profile of the ablation remaining to be accomplished.

19. The method of claim 18, wherein the adjusting comprises reassigning a locally exceeding part of the first subset to the second subset.

20. The method of claim 18, wherein the adjusting comprises reallocating aberrations between the subsets so as to eliminate any locally exceeding parts of the subset.

* * * * *